United States Patent
Ghia et al.

(10) Patent No.: US 10,463,712 B2
(45) Date of Patent: Nov. 5, 2019

(54) HUMAN CATESTATIN INDUCES GUT MICROBIOTA DYSBIOSIS

(71) Applicant: University of Manitoba, Winnipeg (CA)

(72) Inventors: Jean-Eric Ghia, Winnipeg (CA); Mohammed Fazle Alam Rabbi, Winnipeg (CA); Ehsan Khafipour, Winnipeg (CA); Peris Munyaka, Winnipeg (CA)

(*) Notice: Subject to any disclaimer, the term of this patent is extended or adjusted under 35 U.S.C. 154(b) by 0 days.

(21) Appl. No.: 15/569,045

(22) PCT Filed: Apr. 25, 2016

(86) PCT No.: PCT/CA2016/050477
§ 371 (c)(1),
(2) Date: Oct. 24, 2017

(87) PCT Pub. No.: WO2016/176760
PCT Pub. Date: Nov. 10, 2016

(65) Prior Publication Data
US 2018/0125927 A1    May 10, 2018

Related U.S. Application Data

(60) Provisional application No. 62/155,572, filed on May 1, 2015.

(51) Int. Cl.
| | | |
|---|---|---|
| *A61K 38/04* | (2006.01) | |
| *A61K 38/16* | (2006.01) | |
| *A61K 38/00* | (2006.01) | |
| *C07K 14/00* | (2006.01) | |
| *A61K 38/17* | (2006.01) | |
| *C07K 14/575* | (2006.01) | |

(52) U.S. Cl.
CPC ........ *A61K 38/1709* (2013.01); *C07K 14/575* (2013.01)

(58) Field of Classification Search
CPC .... A61K 38/1709; A61K 38/04; A61K 38/00; A61K 38/16; C07K 14/575; C07K 14/00
USPC .......................... 514/2.4, 21.4; 530/300, 326
See application file for complete search history.

(56) References Cited

FOREIGN PATENT DOCUMENTS

WO    2014188373    11/2014

OTHER PUBLICATIONS

Rabbi, M.F. et al, Catestatin decreases macrophage function in two mouse models of experimental colitis, 2014, Biochem, Pharmacol 89(3): 386-398, ISSN 1873-2968.
Shooshtarizadeh, P. et al., The antimicrobial peptides derived from chromogranin/secretogranin family, new actors of innate immunity, 2010, Rgul Pept. 165(1): 102-110, ISSN 1873-1686.

*Primary Examiner* — Julie Ha
(74) *Attorney, Agent, or Firm* — Michael R. Williams; Ryan W. Dupuis; Ade & Comapny Inc.

(57) ABSTRACT

Treatment with catestatin changes the proportion of two major phyla Bacteroidetes and Firmicutes in the gut microbiota in an opposite manner observed in intestinal disorders like IBD, IBS or non-intestinal disorders like obesity. Specifically, administration of an effective amount of catestatin increased the relative percentage of Bacteroidetes and decreased the relative percentage of Firmicutes in the gut microbiota.

18 Claims, 9 Drawing Sheets
Specification includes a Sequence Listing.

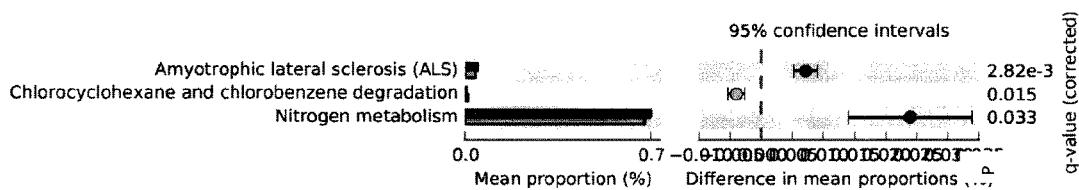

Figure 9. Subsystems and pathways enriched or decreased within the CTS or (Control) mice fecal samples. Corrected P-values were calculated using the Storey FDR correction. Subsystems or pathways overrepresented in the CTS or Control mice fecal samples have a positive or (negative) difference between mean proportions and are indicated by purple or (orange) coloring respectively.

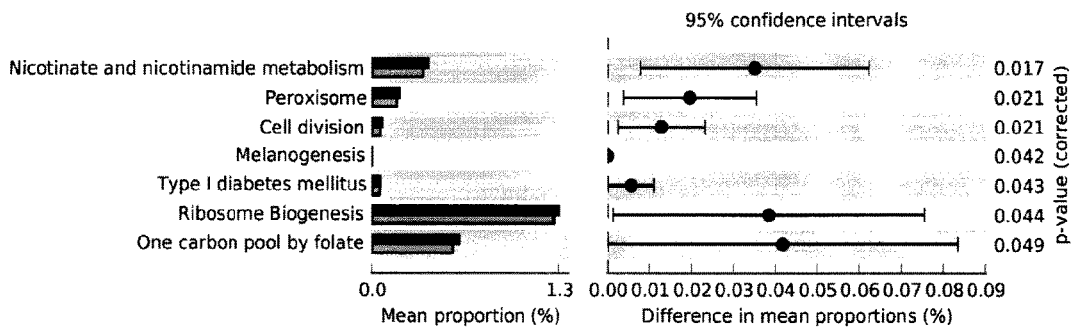

Figure 10. Subsystems and pathways enriched or decreased within the CTS or (Control) mice colon samples. Subsystems or pathways overrepresented in the CTS or Control mice colon samples have a positive or (negative) difference between mean proportions and are indicated by Purple or (orange) coloring respectively.

HUMAN CATESTATIN INDUCES GUT MICROBIOTA DYSBIOSIS

PRIOR APPLICATION INFORMATION

The instant application is a 371 of PCT Application CA2016/050477, filed Apr. 25, 2016, which claims the benefit of U.S. Provisional Patent Application 62/155,572, filed May 1, 2015.

BACKGROUND OF THE INVENTION

Over the last 15 years, bacterial multi-drug resistance (MDR) has emerged and it has several socio-economical causes, from the use of surface antibacterial agents that are now available in many household products[1] to antibiotic over-prescription or failing to complete a course of antibiotics[1]. Although due to MDR new lines of antibiotics are required, the development of new antibiotics has been reduced by pharmaceutical companies because of the cost and complexity of clinical trials[2]. Currently, there are relatively few new antimicrobials in development.

The gastrointestinal tract is heavily colonized with an average of $10^{14}$ microbes that represent thousands of species, which is 10 times more than the total number of cells in the human body[3]. More than 90% of this bacterial population falls under two major phyla: Bacteriodetes (a gram-negative phylum) and Firmicutes (a gram-positive phylum)[4, 5], while the remaining belong to phyla such as Proteobacteria, and Actinobacteria[4, 5]. In healthy individuals, microbial diversity in the intestine is stable over time and demonstrates a symbiotic relationship with the host[3], but a shift in microbial composition, named dysbiosis, targeting mainly Firmicutes and Bacteroidetes, has been described in several pathologies, including related and non-related gastrointestinal pathologies[6-8]. For example, microbial dysbiosis in gut is observed in intestinal disorders like intestinal bowel syndrome (IBS), intestinal bowel disease (IBD) and also non intestinal disorders like obesity and type 1 and type-2 diabetes. Specifically, gut microbiota helps to digest food items and various metabolites and chemicals are produced by the resident microbiota, which plays a significant role in host health or disease state. For example, *Bacteroides thetaiotaomicron* can activate the toll-like receptors (TLRs) in the gut epithelium, which in turn can affect the expression of antimicrobial peptides, such as angiogenins[9, 10]. In addition to the innate immune system, gut microbiota can also control the host's adaptive immune system through T cell receptor αβ-positive intraepithelial lymphocytes, regulatory T cells and T helper 17 cells[5]. Overall, gut homeostasis is largely dependent on the normal gut microbiome[11].

At the mucosal level the epithelium plays a major role in limiting the passage of bacteria to the sub-mucosa and restricts the presence of bacteria to the gut lumen; cell division is an important factor when the epithelial cells are altered and the epithelium needs to be regenerated[12,13]. Antimicrobial peptides (AMPs) secreted by epithelial cells have a broad spectrum effect against bacteria and they are part of an ancient defense mechanism that is present in virtually all mammals[14]. In the gastrointestinal tract, specialized intestinal epithelial cells or circulating inflammatory cells are a major source of these AMPs[14]. Within the epithelium, Paneth cells are the main producer of AMPs but new data indicate that enterochromaffin (EC) cells can hypothetically also produce certain types of AMPs[15].

The EC cells are the major source of chromogranin A (CgA)[16], a family of highly acidic proteins. The CgA gene is localized at 14q32 in the human genome, consisting of 8 exons and 7 introns, and its 2-Kb transcript is translated into the 457-residue CgA protein. The overall homology for CgA in different vertebrates is approximately 40%, but the most highly conserved regions occur at the N- and C-termini, which show up to 88% sequence homology. Cell- and tissue-specific CgA processing has been described in the rat, mouse and human GI tract[17-19]. The CgA primary structure from its cDNA sequence shows the presence of numerous pairs of basic amino acids. These are potential sites for cleavage by prohormone convertases (PC) ⅓ or 2, and carboxypeptidase E/H[2], which is consistent with evidence that CgA may serve as a prohormone for shorter bioactive fragments[21]; this is also suggested by the high sequence conservation of CgA-derived peptides. But in the gut, peptides can be highly sensitive to enzymes present in the luminal environment. Proteolytic fragments of CgA-derived peptides exert a broad spectrum of regulatory activities on the cardiovascular, endocrine and immune systems. Among its highly conserved C-terminal regions, CgA gives rise to a peptide of biological importance: the antihypertensive peptide catestatin (human CTS; $CgA_{352\text{-}372}$)[22-24], which has restricted antimicrobial activity against *Staphylococcus aureus* in vitro[25]. Similar to other AMPs, CTS can interact with anionic components of fungi and viruses. As a result, the microbial membrane is permeabilized, leading to cell lysis[26]. In vitro studies have demonstrated that CTS is effective against gram-positive bacteria such as *Staphylococcus aureus* and group A *Streptococcus*, gram-negative bacteria such as *Escherichia coli* and *Pseudomonas aeruginosa*, yeasts such as *Candida albicans* and filamentous fungi such as *Aspergillus niger, A. fumigates* and *Trichophyton rubrum*[26, 27]. However, to date, there has been no indication that the in vitro data can be reproduced using an in vivo model, as due to the presence of several enzymes located in the gut lumen, CTS peptide can be rapidly inactivated. Moreover, there is no indication about the type of microblota affected, as the colonic mucosa associated population differs completely for the population present in the feces.

Despite the close association between CTS and *Staphylococcus aureus, Escherichia coli* and *Pseudomonas aeruginosa* in vitro, the effects of in vivo CTS treatment on the different type of gut microbiota are unknown. Our aim was to assess the composition of fecal and colonic mucosa associated microbiota and functional alterations in mice that were exposed to CTS for 6 days.

SUMMARY OF THE INVENTION

According to a first aspect of the invention, there is provided a method for increasing levels of Bacteroidetes relative to levels of other bacteria in the gut of an individual in need of such treatment comprising administering to said individual an effective amount of catestatin (CTS).

According to a further aspect of the invention, there is provided a method for decreasing relative levels of Firmicutes relative to other bacteria in the gut of an individual in need of such treatment comprising administering to said individual an effective amount of catestatin (CTS).

According to yet another aspect of the invention, there is provided use of catestatin (CTS) for increasing levels of Bacteroidetes relative to levels of other bacteria in the gut of an individual in need of such treatment.

According to still another aspect of the invention, there is provided use of catestatin (CTS) for decreasing relative levels of Firmicutes relative to other bacteria in the gut of an individual in need of such treatment.

According to a yet further aspect of the invention, there is provided a method of modulating gut microbiota composition comprising administering to an individual in need of such treatment an effective amount of catestatin (CTS).

According to a still further aspect of the invention, there is provided use of catestatin (CTS) for modulating gut microblota composition.

According to another aspect of the invention, there is provided a method of treating or preventing or prophylactically treating type 1 diabetes, type 2 diabetes, obesity, IBS or IBD in an individual in need of such treatment comprising administering to said individual an effective amount of catestatin (CTS).

According to a further aspect of the invention, there is provided use of catestatin (CTS) for treating or preventing or prophylactically treating type 1 diabetes, type 2 diabetes, obesity, IBS or IBD in an individual in need of such treatment.

BRIEF DESCRIPTION OF THE DRAWINGS

FIG. 9. Subsystems and pathways enriched or decreased within the CTS or (Control) mice fecal samples. Corrected P-values were calculated using the Storey FDR correction. Subsystems or pathways overrepresented in the CTS or Control mice fecal samples have a positive or (negative) difference between mean proportions and are indicated by purple or (orange) coloring respectively.

FIG. 10. Subsystems and pathways enriched or decreased within the CTS or (Control) mice colonic mucosa associated samples. Subsystems or pathways overrepresented in the CTS or Control mice colonic mucosa associated samples have a positive or (negative) difference between mean proportions and are indicated by Purple or (orange) coloring respectively.

DESCRIPTION OF THE PREFERRED EMBODIMENTS

Figure 1:
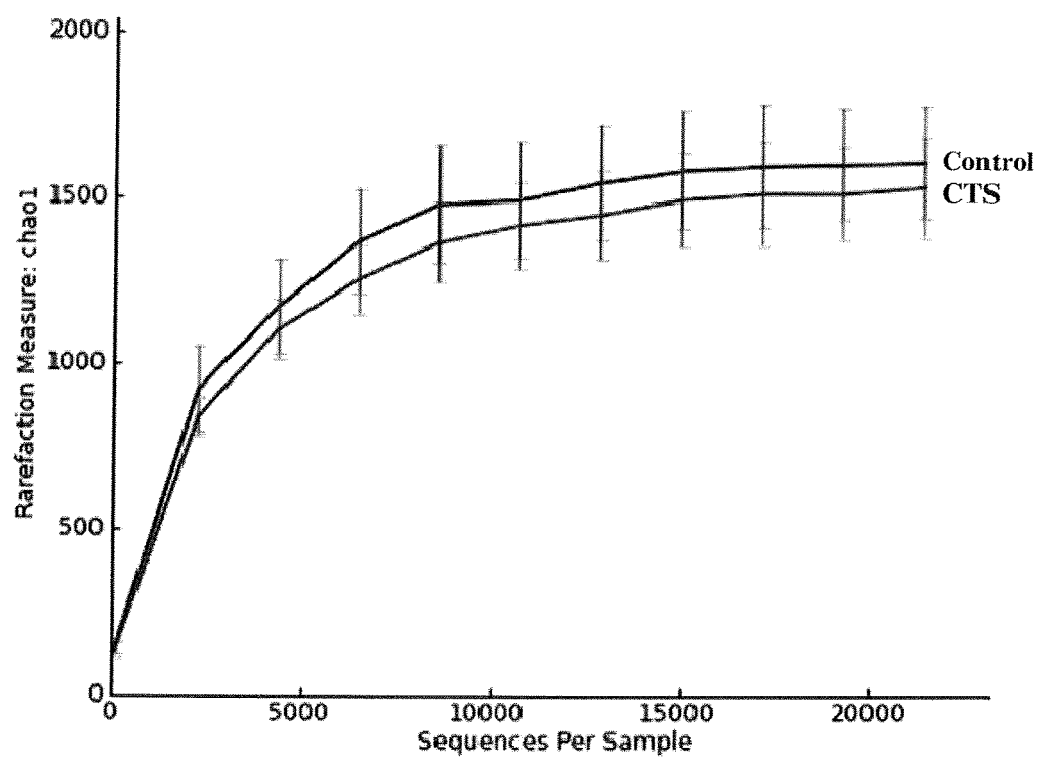
FIG. 1: Rarefaction analysis on Chao 1, a measure of species richness based on operational taxonomic unit (OTU), for the fecal samples; control and CTS. Control and CTS treated mice fecal samples are more diverse compared to DSS and DSS+CTS mice treated samples, which have a low diversity. Diversity is not significantly affected by CTS treatment.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The mammalian intestinal tract is heavily colonized with a dense, complex and diversified microbial population. In healthy individuals, host and gut microbiota enjoy a symbiotic relationship by maintaining intestinal homeostasis and an array of epithelial antimicrobial agents is secreted into the gut to promote intestinal homeostasis. Enterochromaffin cells in the intestinal epithelium are a major source of chromogranin A (CgA), which is a pro-hormone and can be cleaved into a shorter bioactive peptide called catestatin (CTS). This study was carried out to evaluate the possible impact of CTS on gut microbiota in vivo using a mouse model. The CTS treatment did not modify the richness of the bacterial species in the fecal and colonic mucosa associated samples; however, the treatment significantly modified the bacterial community composition between the groups. The PLS-DA analysis revealed an association between specific taxa and the CTS-treated group at lower taxonomic levels. The CTS-treated mice had a significantly lower relative abundance of Firmicutes and higher abundance of Bacteroidetes. No significant change at the phylum level was observed in CTS-treated mice colonic mucosa associated samples. However, at lower phylogenetic levels, some bacterial taxa were significantly associated with CTS-treated mice in both fecal and colonic mucosa associated samples. Differences in microbial functional pathways in both fecal and colonic mucosa associated samples were detected. These results support the hypothesis that CTS treatment modulates gut microbiota composition under physiological conditions. Accordingly, these data indicate that CTS can be used to induce gut homeostasis which in turn can prevent, treat or prophylactically treat diseases such as obesity, type 1 diabetes, type 2 diabetes, inflammatory bowel disease (IBD), inflammatory bowel syndrome (IBS) or other health conditions.

As used herein, "CTS" refers to the antihypertensive peptide catestatin (human CTS). The CTS is derived from amino acids 352-372 chromogranin A (CgA), a family of highly acidic proteins. In some embodiments, CTS has the amino acid sequence SSMKLSFRARAYGFRGPGPQL (SEQ ID NO:1) although variants of this sequence, both naturally occurring and recombinant, may be used within the invention.

Rabbi et al. (2014, Biochem. Pharma. 89: 386-398) teaches that CTS is increased during colitis and that CTS modulates intestinal inflammation via the macrophage population and through a STAT-3 dependent pathway. Specifically, treatment with full length CTS (amino acids 352-372), proximal CTS fragment (amino acids 352-366) and distal CTS fragment (amino acids 360-372) resulted in less severe induced colitis, which indicates that CTS and the fragments thereof can be used to treat intestinal inflammation.

As will be appreciated by one of skill in the art, this indicates that treatment with CTS or either the proximal or distal fragment thereof will reduce inflammation in an individual suffering from colitis. Specifically, it is believed that CTS influences macrophage production of cytokines, which in turn reduces inflammation. Antigen presenting cell like macrophages, are one of the main producer of proinflammatory cytokines. CTS blocks the intracellular pathway implicated in the regulation of proinflammatory cytokines (i.e. IL-1b, IL-6).

Consequently, Rabbi et al. (2014) teaches that CTS can be used to reduce intestinal inflammation in an individual, which in turn would be expected to reduce the severity of symptoms associated with a colitis attack and/or reduce the frequency of colitis episodes.

However, this anti-inflammatory activity is separate and distinct from the known antimicrobial activity of CTS, which had previously only been demonstrated in vitro.

Rabbi et al. (2014) further speculates that intrarectal infusion of CTS peptides might induce a beneficial gut microbiota dysbiosis, which subsequently can affect the development of colitis.

As discussed above, in vitro studies have demonstrated that CTS is effective against gram-positive bacteria such as *Staphylococcus aureus* and group A *Streptococcus*, gram-negative bacteria such as *Escherichia coli, Pseudomonas aeruginosa*, yeasts such as *Candida albicans* and filamentous fungi such as *Aspergillus niger, A. fumigates* and *Trichophyton rubrum*[26, 27]. However, previously, there had been no indication that the in vitro data can be reproduced using an in vivo model, as due to the presence of several enzymes located in the gut lumen CTS peptide can be rapidly inactivated. Specifically, there are a number of proteases which can act on serine, cysteine and aspartic amino acids[28]. As the human CTS sequence used in this study has serine and aspartic sequences (SSMKLSFRARAYGFRGPGPQL, SEQ ID No:1), it was anticipated that CTS could be inactivated in the gut.

Specifically, CTS is a cationic peptide and as such the inventors hypothesized that if CTS avoided degradation in the gastrointestinal environment, this peptide might exerts it's effect by electrostatic interactions with the negatively charged phospholipid microbial cell walls. As a result of these interactions, any suitable microbial membrane that CTS could interact with would be disrupted. It was further anticipated that CTS could have a general effect, for example, reducing levels of all bacteria.

However, as discussed herein, the gastrointestinal environment in vivo is incredibly complex and it is impossible to predict the exact effect that a general antimicrobial such as CTS would have in the gut, assuming that it was not degraded by the serine and aspartic add proteases. Furthermore, it is simply not possible to create a complex gastrointestinal environment in vitro that has the enormous microbial diversity to sufficiently mimic the in vitro gut.

Furthermore, as discussed below, in fact, *S. aureus* and *E. coli* levels in the gut were not affected by CTS administration in vivo, demonstrating the difference that can be found between in vitro studies and in vivo experiments. As such, it is clear that not all in vitro results can be extrapolated to in vivo analysis, especially in the context that in vitro, many bacteria are non-cultivable due to the lack of anaerobic condition and are present when the whole microbiome is studied.

Furthermore, as discussed herein, CTS treatment did not modify the richness of the bacterial species in fecal and colonic mucosa associated samples. Specifically, as shown in FIG. 1 and as discussed herein, control and CTS-treated mice treated samples were more diverse than DSS and DSS+CTS mice treated samples, which have a low diversity. These data demonstrated that bacterial diversity or richness was not significantly affected by CTS treatment.

Based on these results, one conclusion would have been that the in vitro anti-microbial activity could not function in vivo, possibly due to protease degradation.

The inventors theorized that coating CTS might prevent or delay degradation; however, there were concerns that the coating would interfere with the antibiotic activity of CTS which, as discussed above, interacts with anionic components of the microbial membrane and permeabilizes the membrane, leading to cell lysis. As will be appreciated by one of skill in the art, there was considerable concern that a suitably protective coating that would protect CTS from the proteases would also prevent CTS from interacting with the negatively charged components of the bacterial membranes.

Another possibility would have been that CTS was having a general or broad spectrum antimicrobial affect.

Figure 4:
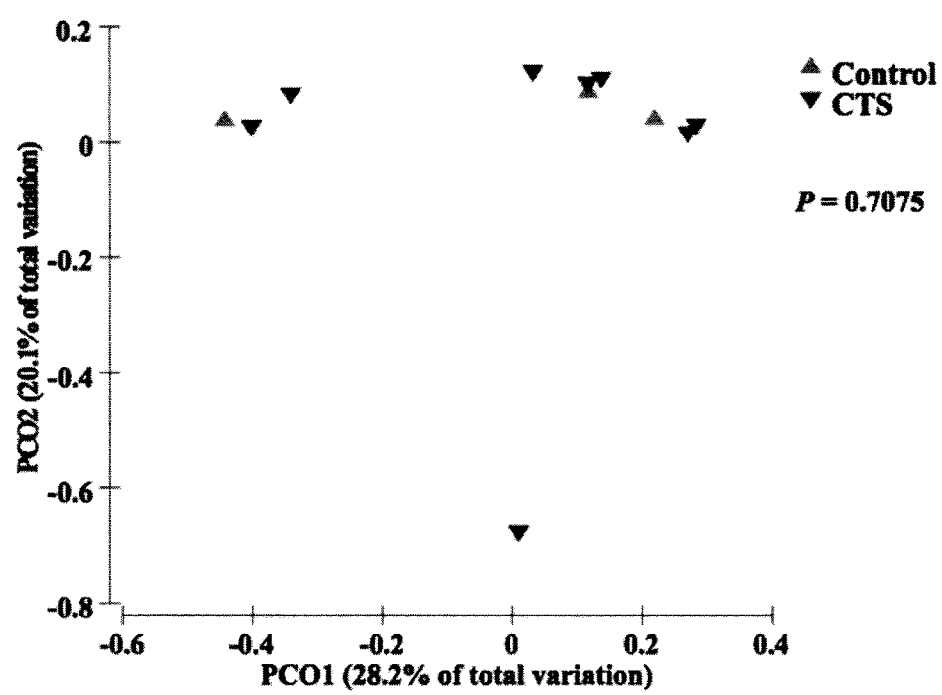
FIG. 4: Principal coordinate analysis (PCoA) based on the weighted and unweighted UniFrac distance metric. Each colored point represents a colonic mucosa associated sample obtained from one mice and it is shaded according to different treatment (CTS or Control). P values were calculated using PERMANOVA. Samples did not cluster according to treatment status of the mice (P>0.05), suggesting that CTS treatment did not significantly change bacterial communities.

As shown in FIG. 4, CTS treatment also did not significantly change the bacterial communities in the colonic mucosa associated samples, as discussed in greater detail below.

Figure 3:
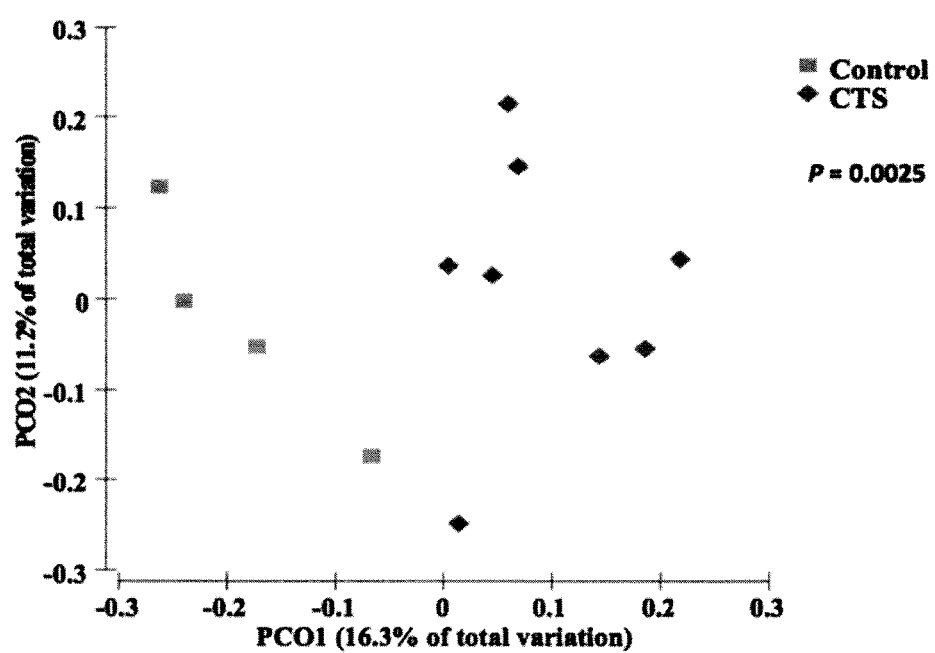
FIG. 3: Principal coordinate analysis (PCoA) based on the unweighted UniFrac distance metric. Each colored point represents a fecal sample obtained from one mice and it is shaded according to different treatment (CTS or Control). P values were calculated using PERMANOVA. Samples clustered according to treatment status of the mice (P<0.05), suggesting that CTS and Control mice fecal samples are composed of distinct bacterial communities.
Figure 5:
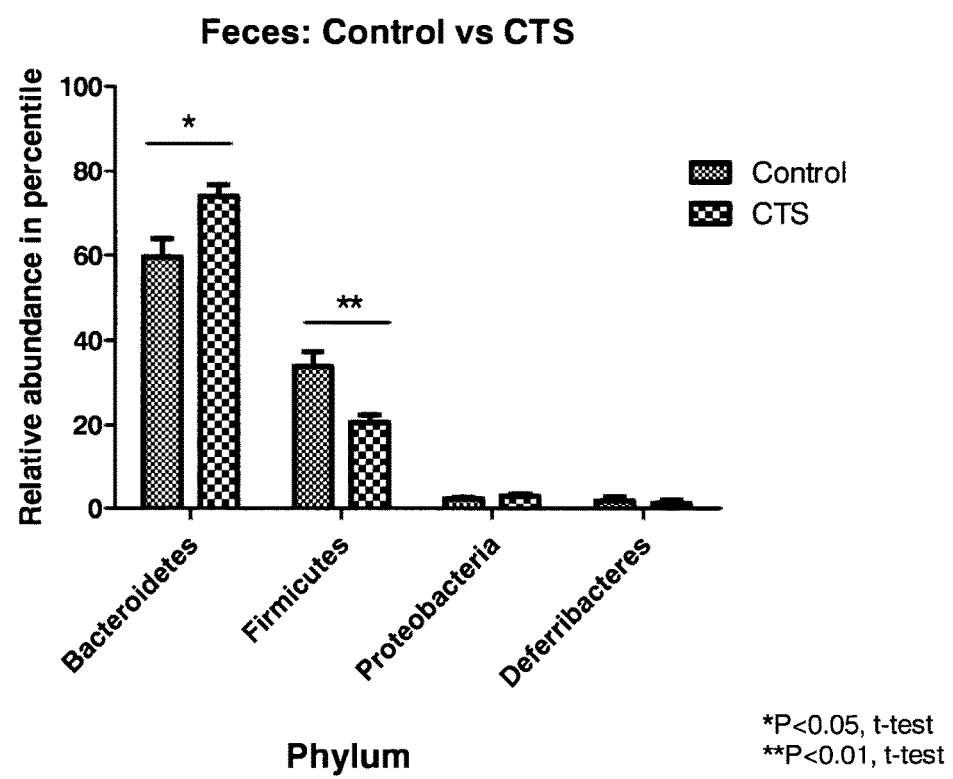
FIG. 5: Effect of CTS treatment on the abundant phyla (≥1%) present in the fecal samples. After quality filtering steps 10 phyla was identified in fecal samples. Among these 4 phyla were considered abundant within the population (≥1%), including Firmicutes, Bacteroidetes, Proteobacteria, and Deferribacteres. CTS treated mice had a significantly higher level of Bacteroidetes population compared to Control (P<0.05, t-test). On the other hand Firmicutes population were lowered significantly in the feces of CTS treated animals (P<0.01, t-test)

However, surprisingly, as shown in FIG. 3, it was determined that CTS and control mice fecal samples were composed of distinct bacterial communities. More significantly, as shown in FIG. 5, CTS treated mice had a significantly higher level of Bacteroidetes compared to the control mice. The CTS treated mice also had a significantly lower level of Firmicutes compared to the control mice. Thus, in the fecal samples, CTS treatment significantly modified the bacterial community composition between the CTS treatment group and the control.

While CTS was not having a specific effect on diversity of the microbiota or in the colonic mucosa associated samples, CTS treatment was having a significant effect on distinct bacterial communities within fecal samples, indicating that coating was not necessary for rectal administration.

This modification or modulation of the gut microbiota for example to increase relative levels of Bacteroidetes Is significant as lower levels of Bacteroidetes may result in adverse health effects as these bacteria have important starch degrading enzymes and also help to establish normal gut immunity. For example, *B. thetaiotaomcron* prevents activation of the proinflammatory transcription factor NFkβ[41]. Bacteroidetes also help to prevent production of virulent factors from pathogenic *E. coli*[42]. Moreover, there is data showing that fecal transplantation from a healthy person to IBD patients helps to reduce the symptoms[43, 44] and that administration of probiotics which modify the microbiota can improve IBS and IBD.

Described herein is a method for increasing levels of Bacteroidetes relative to levels of other bacteria in the gut of an individual in need of such treatment comprising administering to said individual an effective amount of catestatin (CTS).

Described herein is a method for decreasing relative levels of Firmicutes relative to other bacteria in the gut of an individual in need of such treatment comprising administering to said individual an effective amount of catestatin (CTS).

Also described herein is the use of catestatin (CTS) for increasing levels of Bacteroidetes relative to levels of other bacteria in the gut of an individual in need of such treatment.

Also described herein is the use of catestatin (CTS) for decreasing relative levels of Firmicutes relative to other bacteria in the gut of an individual in need of such treatment.

Also contemplated is a method of modulating gut microbiota composition comprising administering to an individual in need of such treatment an effective amount of catestatin (CTS).

The use of catestatin (CTS) for modulating gut microbiota composition is also contemplated.

As will be appreciated by one of skill in the art and as discussed herein, an "effective amount" is an amount which is sufficient to achieve the desired result, that is, modulating the gut microbiota composition of an individual, for example, increasing the relative percentage or proportion of Bacteroidetes relative to other bacteria within the gut microbiota and/or decreasing the relative percentage or proportion of Firmicutes relative to other bacteria within the gut microbiota. Such an effective amount will of course depend on the severity of the dysbiosis within the gut microbiota of the individual, as well as other factors, such as the age, weight and general condition of the individual. Determination of such an effective amount is considered to be within the routine skill of one knowledgeable in the art.

The effective amount may be administered by a variety of means, as discussed below and may be administered on a schedule, for example, daily, every other day or multiple times a day, again depending on the state of the individual being treated.

As used herein, an "individual in need of such treatment" is an individual whose gut microbiota is in a dysbiotic state or who is thought to have developed dysbiosis or is at risk of developing dysbiosis.

For example, the individual may have developed dysbiosis as a result of another treatment or as a result of being subjected to a particular diet or environmental conditions. Alternatively, the individual may be an individual who is at risk of developing type 1 diabetes, type 2 diabetes, obesity, IBS or IBD either as a result of heredity, genetic predisposition and/or lifestyle.

Described herein is a method of treating or preventing or prophylactically treating type 1 diabetes, obesity, IBS or IBD in an individual in need of such treatment comprising administering to said individual an effective amount of catestatin (CTS).

Also described herein is the use of catestatin (CTS) for treating or preventing or prophylactically treating type 1 diabetes, type 2 diabetes, obesity, IBS or IBD in an individual in need of such treatment.

Preferably, the CTS is human CTS.

In some embodiments, the CTS comprises the amino acid sequence as set forth in SEQ ID NO:1 (SSMKLSFRA-RAYGFRGPGPQL) or a variant thereof which retains antimicrobial activity.

As used herein in regards IBS or IBD, an "effective amount" of CTS is an amount of CTS that is sufficient to reduce one or more symptoms associated with IBD (inflammatory bowel disease) or IBS (irritable bowel syndrome). Specifically, this "effective amount" will be sufficient to reduce the severity of one or more symptoms associated with IBD or IBS, for example, abdominal cramps, abdominal pain, diarrhea, fever, weight loss, loss of appetite, bloating and vomiting. The "effective amount" may also reduce the frequency of attacks of IBD and/or IBS and the severity of these symptoms and may also increase the length of time between symptoms, as will be apparent to one of skill in the art.

It can be postulated that there is a bilateral communication between the gut microbiota and mucosal cells present in the inflamed mucosa. However, to date although numbers of studies have been performed using all the anti-inflammatory drug presents on the marker, none have demonstrated a direct or indirect effect on the gut microbiota. Therefore, we can speculate that treating inflammation in gastrointestinal related disorders will not inherently treat dysbiosis.

Conversely, it has been demonstrated that pre- or probiotics and the use of some antibiotic can modify the gut microbiota and modify symptoms associated with IBD and IBS. This demonstrates that treating the underlying disease, gut dysbiosis, can subsequently modify the symptoms associated to mucosal inflammation. In our context, the treatment with CTS will modify gut dysbiosis and ultimately lead to a correction of mucosal inflammatory-associated symptoms.

As will be appreciated by one of skill in the art, the prior teaching of CTS as effective at reducing inflammation during colitis indicates that CTS could be administered during a colitis attack to reduce the severity of symptoms caused by the inflammation and more specifically by immune cell represented by the macrophages population. However, this does not teach or suggest that CTS could be used to correct or treat dysbiosis or prophylactically treat IBD or IBS. Furthermore, it does not teach or suggest treatment or prophylactic treatment or prevention of obesity, type 1 diabetes or type 2 diabetes.

Accordingly, in another aspect of the invention, the use of CTS to treat or prevent IBD or IBS is contemplated with the proviso that symptoms other than inflammation are being treated.

In other embodiments, CTS is administered to an individual suffering from or at risk of developing IBD or IBS to treat dysbiosis associated with IBD or IBS by increasing levels of Bacteroidetes relative to levels of Firmicutes in the gut of said individual.

Preferably, the CTS is formulated for rectal administration to the individual in need of such treatment.

Typically, active agents are delivered rectally by suppository, enema, ointment, cream, foam or injection.

Suppositories are generally fatty in nature but water-soluble or water-miscible bases can also be used.

Typically, enemas comprise the active agent dispersed in a suitable flowable carrier vehicle, such as water, alcohol or an aqueous-alcohol fluid. The carrier may be thickened with natural and/or synthetic thickeners such as gums, acrylates or modified celluloses. Unit dosages of enema formulations can be administered from prefilled bags or syringes.

Foams may include a foaming agent such as n-butane, propane or i-butane. Such foam formulations may be delivered from a pressurized container.

Suitable excipients for rectal administration include but are by no means limited to preservatives, surfactants, emulsifiers, mineral oils, propellants, thickening agents, lubricants, preservatives, pH adjusting agents, chelating agents, emollients and/or humectants, permeation enhancers, suspension-forming agents or mucoadhesive agents.

In some embodiments, the effective amount of CTS If formulated as a suppository or enema.

The mammalian intestine continuously encounters more microorganisms than any other tissue, and survival of the mammalian population largely depends on their unique adaption in the world of microorganisms. Specific intestinal epithelial cells release several antimicrobial peptides, which are critical for maintaining a stable ecological environment that favors commensal and targeting pathological microorganisms[37]. Moreover, these are also important for Inhibiting ongoing Inflammatory responses. CTS, a highly conserved CgA peptide that is present in Intestinal EC cells, was shown to be an peptide with some Immunomodulatory activities and restricted in vitro antibacterial activities[38], but also antifungal and antiviral activity[26, 27]. However, to date, and due to the presence of several enzymes present in the gut lumen, there are no documented studies that demonstrate the effect of this peptide on gut microbiota using in vivo models. Here, it is shown that i.r. administration of CTS modulates gut microbiota composition under physiological conditions.

Based on the α-diversity, it was observed that richness and the bacterial population diversity in both fecal and colonic mucosa associated samples did not change after CTS administration. However, β-diversity analysis using the unweighted Unifrac distances through QIIME revealed that CTS-treated mice had a fecal microbial composition that was significantly separated from the control group, suggesting that a short-term exposure of this peptide in the gut might change the microbial composition profile. This is in accordance with studies demonstrating the effect of other antibacterial peptide released by Paneth cells (i.e. defensin) on gut microbiota[39].

Recent investigation shows that intestinal inflammatory conditions such as inflammatory bowel disease (IBD) or inflammatory bowel syndrome (IBS) are associated with altered intestinal homeostasis[7, 40]. Although microbial dysbiosis has been suggested to be a cause of intestinal pathophysiological conditions, this is still controversial. However, it has been observed that microbial diversity is significantly altered in human and animal models of IBS[7, 40]. In the context of IBS, although an exact causal microbe has not yet been identified, a reduction in the microbial diversity has been documented and this temporal gut microbiota instability can result in altered host physiology, resulting in heterogeneous symptoms such as those observed in IBS patients[7, 40]. At the phylum level, IBS patients have a higher relative abundance of Firmicutes and lower abundance of Bacteroidetes compared to controls[7].

In this study, it was observed that CTS treatment is significantly associated with a relative reduction of Firmicutes in the feces compared with saline-treated mice. Conversely, CTS treatment was associated with a significant higher relative abundance of Bacteroidetes in the feces compared with saline-treated mice. Besides IBS, in colitic conditions, studies demonstrated a reduction in relative abundances of Bacteroidetes[45] and Verrucomicrobia[45], a group of bacteria that is present in low numbers in the mammalian intestine, and which are able to degrade mucin[46], suggesting for a shift in the microbial community. In this study, it was observed that CTS treatment lowered Verrucomicrobia in both fecal and colonic mucosa associated samples. In this study, CTS treatment did not significantly change the relative abundance of Proteobacteria in mice, but a reduction in members of this phylum in colonic mucosa associated samples was observed. In addition to colonic mucosa associated pathologies, studies showed that Firmicutes is significantly more abundant relative to Bacteroidetes in obese mice compared to lean mice[8]; these results were also observed in humans[8]. In this study, CTS treatment was associated with a significant abundance of Bacteroidetes relative to Firmicutes in fecal samples, which was opposite to results from obese animals and humans. However, this change in Bacteroidetes and Firmicutes abundance were not observed in the colonic mucosa associated samples, suggesting that prolonged administration of this peptide might be required to observe a possible change in the colon wall. At the lower taxonomical level, CTS administration was associated with significant increase in *Prevotella, Bacteroides*, and *Parabacteroides* populations in the feces. A recent meta-analysis (Walters et al, FEBS Letters 588 (2014) 4223-4233) of gut micrbiome in patients with ulcerative colitis, colonic Crohn's disease or ileal Crohn's disease indicated that these three populations were significantly depleted in patients with ulcerative colitis and Crohn's disease and that these genera are among the signature taxa that can be used to predict if a subject likely has IBD or not. It is, therefore, very interesting that CTS supplementation could enrich the population of *Prevotella, Bacteroides*, and *Parabacteroides*, which are significantly depleted in IBD patients.

As discussed above, as CTS is cationic in nature, it was expected that there would be a broad spectrum antimicrobial activity, or, if the peptide was not able to 0.15 remain active in gastrointestinal environment, that there would be no effect.

As will be appreciated by one of skill in the art, it is impossible to create a complex gastrointestinal environment in vitro with enormous microbial diversity. But the illumina sequencing technique targeting bacterial 16s rRNA provided the overall impact of CTS on gut microbiota in the actual gastrointestinal environment Although the overall microbial richness was not modified, it has been shown for the first time that CTS treatment changed the proportion of two major phyla Bacteroidetes and Firmicutes in the feces in an opposite manner observed in intestinal disorders like IBD, IBS or non-intestinal disorders like obesity and type 1 and type 2 diabetes.

The CTS treatment also caused microbial changes in lower taxonomic levels. Using our current approach, we classified microbes to the genus level. It was observed that certain bacterial taxa were positively associated with CTS treatment in both the fecal and colonic mucosa associated samples. Among these taxa, *Bacteroides* (genus) and *Parabacteroides* (genus) showed a positive association with CTS treatment in the fecal samples. Both of these belong to the Bacteroidales order, which also showed a positive association with CTS treatment in the colonic mucosa associated samples. *Bacteroides* and *Parabacteroides* species represent ~25% of the colonic mucosa associated microbiota and are commensal to the host when present in the guts. These anaerobic rods can transform simple and complex sugars into volatile fatty acids, which can be absorbed by the large intestine as a nutrient. *Bacteroides thetaiotaomicron* has several starch-binding genes and can produce significant amount of glycosylhydrolases, which can be crucial to prevent obesity[49]. This might explain why Bacteroidetes are more abundant in obese mice compared to lean mice. Besides the enormous starch-utilizing capacity, *Bacteroides* species are important for developing gut immunity. For example, *B. thetaiotaomicron* can stimulate Paneth cells to produce Paneth cell protein (Ang4), which is lethal to certain pathogenic microorganisms (e.g. *Listeria monocytogenes*)[34]. In addition, *B. fragilis* produces zwitterionic polysaccharide (ZPS), which is important for developing CD4 T cells. ZPS-activated CD4 T cells produce interleukin-10 (IL-10), which is essential to prevent abscess formation and other unchecked inflammatory responses[49-51]. Increased *Bacteroides* population in mice in response to CTS exposure might be beneficial to control obesity and inflammatory conditions such as IBD or IBS. These results might also explain the underlying mechanisms for improving gut inflammation that we observed previously in colitic mice exposed to CTS[30].

In this study, metagenomic functional prediction analysis was performed. This approach helps to connect the microbiota as a whole to specific functions in the environment[52]. Using this approach, it was observed that certain subsystems or pathways are enriched after CTS treatment in both the fecal and colonic mucosa samples, surprisingly suggesting that although we were not be able to see any effect for some markers studied after 6 days treatment with CTS, CTS treatment can modify specific functions in the environment. One of the most important observations was increased cell division in the CTS-treated mice. In physiological and pathophysiological conditions, the mammalian intestine needs to constantly replenish its epithelial tissues, which are at risk of continuous environmental attacks such as oxidative stress, microbial antigens or inflammatory mediators. Increased cell division stimulated by CTS treatment might help to reverse the damage to the intestine caused by increased inflammation[53].

Surprisingly, beside the fact that the purpose of the study was to define the effect of CTS on gut bacteria and it potential Implication in gut-related diseases, the prediction analysis also demonstrated that CTS treatment Induced functional shifts in the murine intestinal microbiota, with different metabolic pathways that are enriched in the mucosal microbiota of fecal and colonic mucosa associated samples compared to the control mice. CTS treatment showed a positive association with amyotrophic lateral sclerosis (ALS), a condition where the CgA peptide levels are lower in affected patients[54]. However, the exact role of CgA peptides in ALS remains unknown and further data is needed to decipher their exact role in the context of stimulating microglial immune response. Type 1 diabetes was also positively associated with CTS treatment in our study and this observation is in agreement with other studies that demonstrated the abundance of *Bacteroides* in this pathological condition[55]. It was also shown that WE14, a CgA-derived peptide from the distal part of CgA can activate CD4 T cell clones, which can Induce diabetes in vivo[56].

These findings provide new insight into the mechanisms of gut microbiota regulation by CTS. We observed a not predicted shift in the microbial profile in response to CTS treatment, which was more prominent in the feces than in colonic mucosa. These results establish the utility of new anti-microbiota peptides and their use as therapeutic agents to treat several conditions of the gastrointestinal tract, such as IBD, IBS, obesity but also other health conditions, such as ALS, obesity and T1 diabetes.

Results

Descriptive Analysis

Mice were divided into two groups: one group (control) was Injected i.r. with normal saline while the other group received CTS (1.5 mg/kg/day, i.r. for 6 days). Weight loss, stool consistency and blood in the feces were determined every day for each animal. The peptide itself had no direct effect on these parameters, which is consistent with our previous findings[30].

Sample Assessment by Illumina Sequencing

After sacrifice, we collected fecal and colonic mucosa associated samples from a total of 12 mice. Among these, the control group received normal saline intrarectally and the others received CTS intrarectally (1.5 mg per kg body weight for 6 days). During the DNA extraction process, one colonic mucosa associated sample from the saline-treated group was discarded because of poor quality or purity, resulting in a total of 12 useable fecal samples and 11 useable colonic mucosa associated samples for Illumina sequencing. For fecal samples, a total of 328,085 sequences were generated. After quality-filtering steps, an average of 27,340.42 high quality sequences per sample was determined. For colonic mucosa associated samples, a total of 207,123 sequences were generated. After quality-filtering steps, an average of 18,829.36 high-quality sequences per sample was determined.

Figure 2:
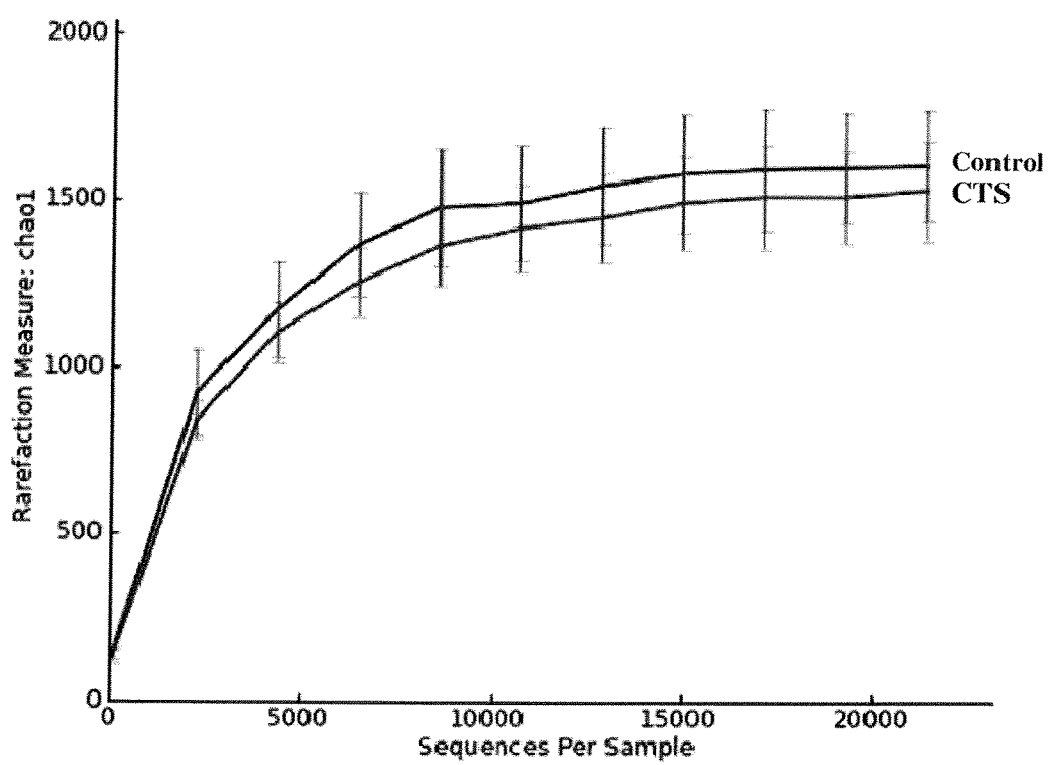
FIG. 2: Rarefaction analysis on Chao 1, a measure of species richness based on operational taxonomic unit (OTU), for the colonic mucosa associated samples; Control and CTS. Diversity is not significantly affected by CTS treatment.

CTS Exposure Did not Significantly Decrease α-Diversity in Fecal and Colonic Mucosa Associated Samples in Mice Bacterial richness and diversity from both fecal and colonic mucosa associated samples between control and CTS-treated groups were calculated. CTS treatment had no significant impact on Chao1, ACE, Shanon and Simpson indices of α-diversity in fecal or colonic mucosa associated bacterial community composition (FIGS. 1 and 2).

CTS Treatment Significantly Influenced β-Diversity in Focal Samples but Did not Significantly Influence Colonic Mucosa Associated Samples in Mice Bacterial community composition in the fecal and colonic associated microbiota of control and CTS-treated animals (β-diversity) was determined using PERMANOVA analyses of Bray-Curtis distances (FIGS. 3 and 4). Using unweighted R-diversity, we observed that bacterial communities from fecal samples of CTS-treated mice were clustered separately ($P<0.05$) from controls, suggesting that the treatment modified the fecal bacterial profile (FIG. 3). However, there was no significant change in the bacterial community in colonic mucosa associated samples in CTS-treated mice compared to controls (FIG. 4).

CTS Treatment Influenced Colonic but not Fecal Bacterial Microbiota Composition at the Phylum Level in Mice In the fecal samples, a total of 10 phyla were identified, of which 4 phyla were considered to be abundant within the population (≥1%); these included Firmicutes, Bacteroidetes, Proteobacteria and Deferribacteres. The other six phyla were considered less abundant within the population (<1%), and Included Actinobacteria, Cyanobacteria, Fibrobacteres, TM7, Tenericutes and Verrucomicrobia (Table 1). Among the 4 abundant populations, CTS treatment significantly increased the relative abundance of Bacteroidetes (P<0.05) and significantly decreased the Firmicutes population (P<0.001) in the feces (FIG. 5).

Figure 6:
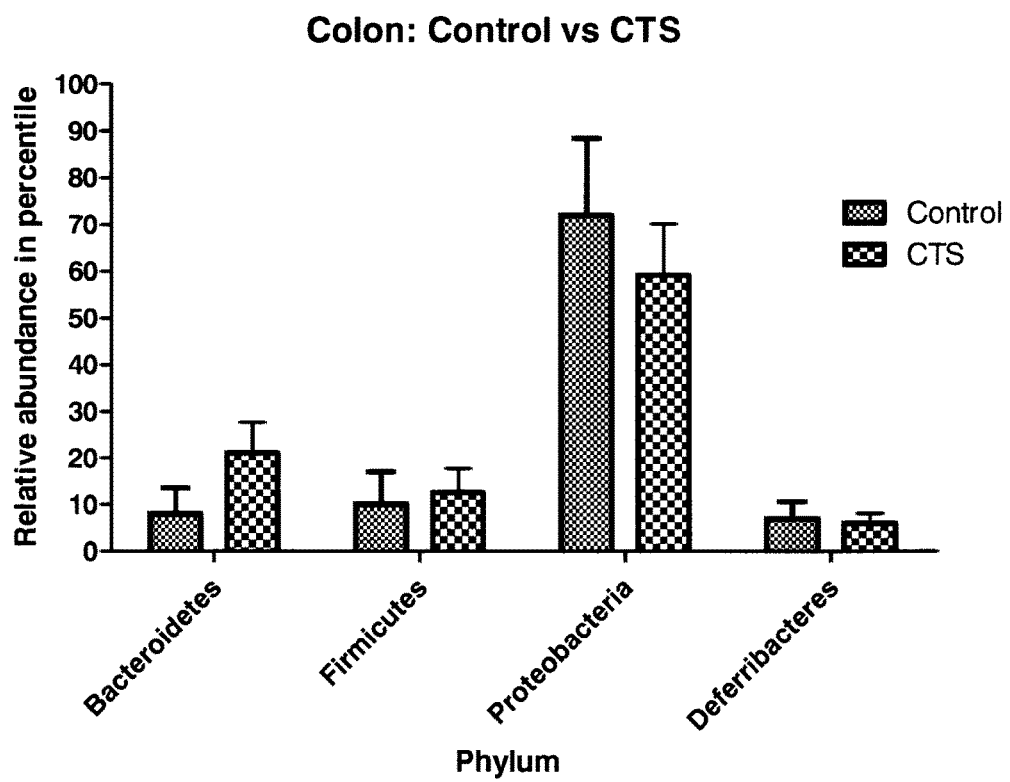
FIG. 6: Effect of CTS treatment on the abundant phyla (≥1%) present in the colonic mucosa associated samples. After quality filtering steps 19 phyla was identified in colonic mucosa associated samples. Among these 4 phyla were considered abundant within the population (≥1%), including Firmicutes, Bacteroidetes, Proteobacteria, and Deferribacteres. CTS treatment did not have a significant impact on these abundant phyla present in the colonic mucosa associated samples.

In the colonic mucosa associated samples, a total of 19 phyla were identified, of which 4 phyla were considered to be abundant within the population; these included Firmicutes, Bacteroidetes, Proteobacteria and Deferribacteres. The other 15 phyla were considered less abundant within the population, and included Acidobacteria, Actinobacteria, Armatimonadetes, Chlamydiae, Chlorobi, Cyanobacteria, Fibrobacteres, Lentisphaerae, OD1, OP3, Planctomycetes, Spirochaetes, TM7, Tenericutes and Verrucomicrobia (Table 2). CTS treatment had no significant impact on the relative abundance of bacterial phyla within the population (FIG. 6).

Figure 7:
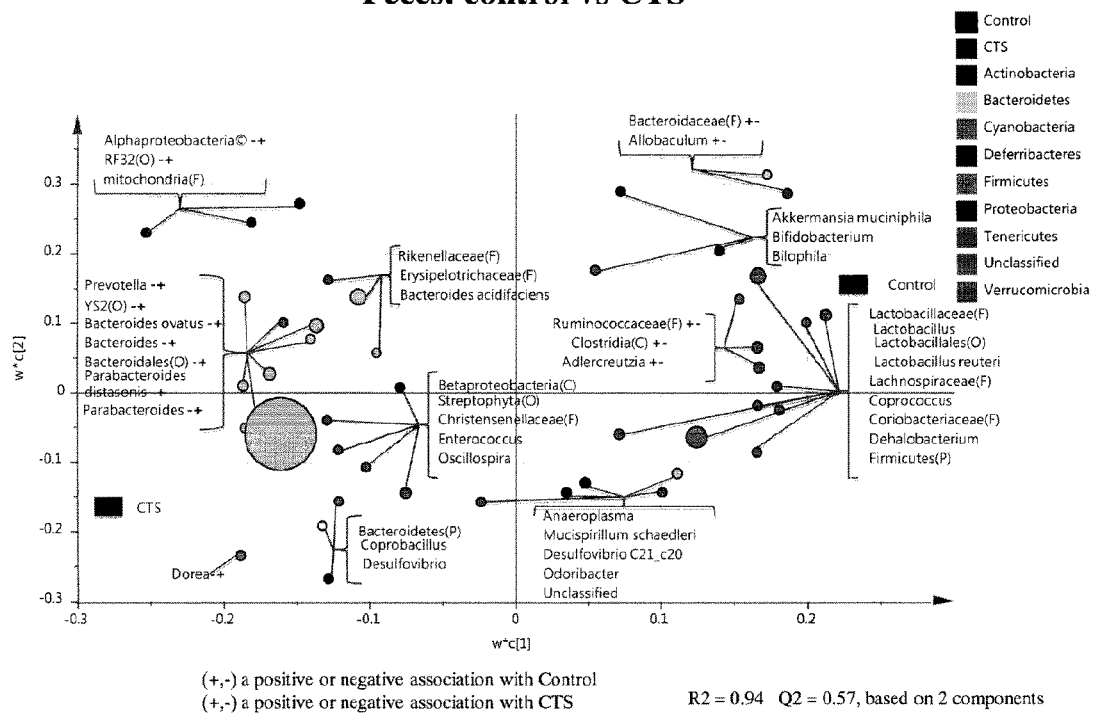
FIG. 7: Partial least square discriminant analysis (PLS-DA) of bacterial communities comparing taxa that were associated with the Control or CTS treatments in the mice fecal samples. All taxa are colored based on the phyla to which they belong. Some sequences could only be affiliated to phylum (P), order (O), family (F) or class (C) levels. Specific taxa were significantly associated with each treatment group, which may be an indicator of shifts in the physiological or metabolic processes that the taxa may influence.

CTS Treatment Influences Fecal Bacterial Microblota Composition at Lower Phylogenetic Levels in Mice A total of 328,085 sequences were generated after quality-filtering steps, with an average of 27,340 high-quality sequences per sample. This resulted in identification of 10 phyla, as shown above, and 86 taxa, but some taxa were only classified up to the Phylum (P), Class (C), Order (O), Family (F), Genus or species level. Of the 86 taxa, 54 taxa were considered abundant within the population, while 32 taxa were considered less abundant within the population. Results of the relative abundance of various genera with percentages of sequences ≥0.01% were analyzed using PLS-DA to identify bacteria that were most characteristic of CTS or Control treatments. The PLS-DA analysis showed that the genera *Prevotella, Bacteroides Ovatus, Bacteroides, Parabacteroides distarosis, Parabacteroides* and *Dorea* were positively associated with the CTS treatment in the fecal samples ($R^2=0.94$, $Q^2=0.57$) (FIG. 7). In addition, members of Alpharoteobacteria (Class), Bacteroidales (Order), RF32 (Order), mitochondria (Family) and YS2 (Order) also showed a positive association with CTS treatment in the fecal samples ($R^2=0.94$, $Q^2=0.57$). A negative association with the members of *Adlercreutzia, Allobaculum*, Bacteroidaceae (Family), Clostridia (Class) and Ruminococcaceae (Family) were evident in the fecal samples collected from CTS-treated mice ($R^2=0.94$, $Q^2=0.57$).

Figure 8:
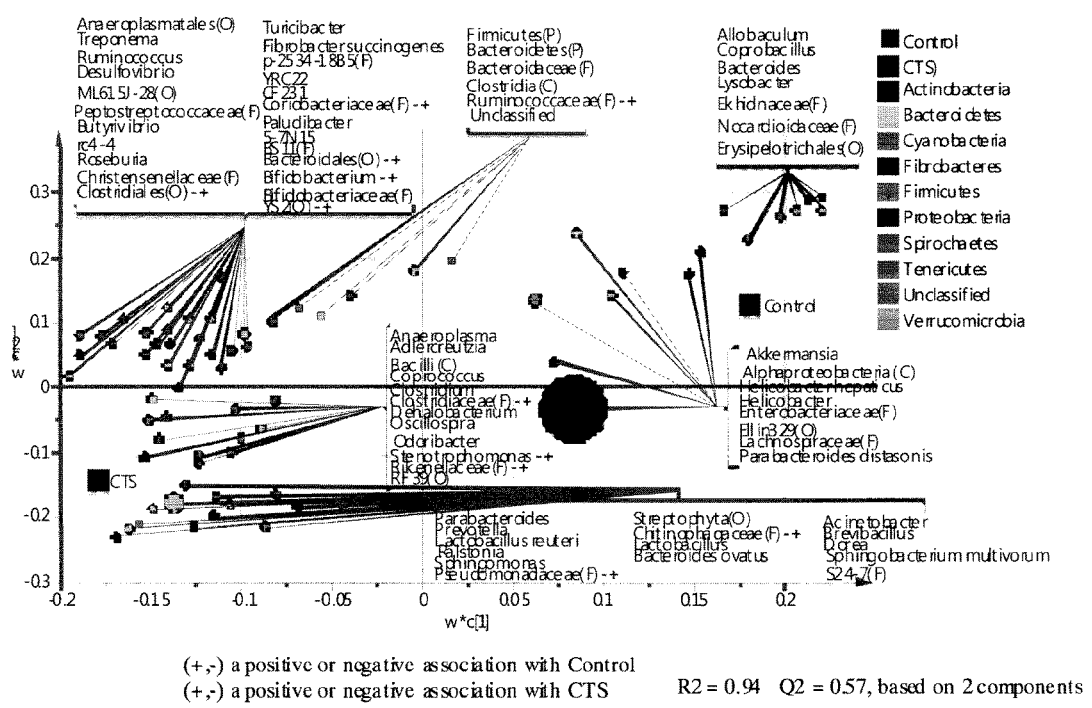
FIG. 8: Partial least square discriminant analysis (PLS-DA) of bacterial communities comparing taxa that were associated with the Control or CTS treatments in the mice colonic mucosa associated samples. All taxa are colored based on the phyla to which they belong. Some sequences could only be affiliated to phylum (P), order (O), family (F) or class (C) levels. Specific taxa were significantly associated with each treatment group, which may be an indicator of shifts in the physiological or metabolic processes that the taxa may influence.

CTS Treatment Influences Colonic Mucosa Associated Bacterial Microbiota Composition at Lower Phylogenetic Levels in Mice A total of 207,123 sequences were generated after quality-filtering steps, with an average of 18,829 high-quality sequences per sample. This resulted in identification of 19 phyla, as shown above, and 179 taxa, but some taxa were only classified up to the Phylum (P), Class (C), Order (O), Family (F), Genus or species level. Of the 179 taxa, 84 taxa were considered abundant within the population, while 95 taxa were considered less abundant within the population. Relative abundance of various genera/taxa of colonic mucosa associated samples with sequence percentages ≥0.01% were analyzed using PLS-DA to Identify bacteria that were most characteristic of the CTS or control treatments. The PLS-DA analysis of the colonic mucosa associated samples showed that genera *Bifidobacterium* and *Stenotrophomonas* had a positive association with the CTS treatment ($R^2=0.32$, $Q^2=0.242$) (FIG. 8). Members of Bacteroidales (Order), Chitinophagaceae (Family), Clostridlaceae (Family), Clostridiales (Order), Coriobacteriaceae (Family), Pseudomonadaceae (Family), Rikenellaceae (Family), Ruminococcaceae (Family) and YS2 (Order) also showed a positive association with the CTS treatment in the colonic mucosa associated samples ($R^2=0.32$, $Q^2=0.242$) (FIG. 8).

CTS Treatment Significantly Influences Fecal and Colonic Mucosa Associated Microblota Functional and Metabolic Pathways in Mice To determine the functional KEGG pathways that could be associated with the observed microbial changes, we compared the functional pathways for the microbiota in fecal and colonic mucosa associated samples from the CTS-treated group with those of the control mice. Several metabolic pathways were determined. Subsystems or pathways that have a significant positive or negative correlation with CTS treatment are shown in FIGS. 9 and 10. In the fecal samples from CTS-treated mice, chlorocyclohexane and chlorobenzene degradation were significantly downregulated (P=0.015) (FIG. 9). However, nitrogen metabolism was enriched in the fecal samples from CTS-treated mice (P=0.033; FIG. 9). Pathways associated with amyotrophic lateral sclerosis (ALS) were significantly enriched in the fecal samples of this group of mice (P=$2.82^{e-3}$). In the colonic mucosa associated samples from CTS treated mice, nicotinate and nicotinamide metabolism, cell division and ribosome biogenesis were significantly enriched compared to the controls (P<0.05; FIG. 10). However, analysis of colonic mucosa associated samples from CTS-treated mice also had a significant positive correlation with type 1 diabetes mellitus (P=0.043; FIG. 10).

Materials and Methods

Animals

Male C57BL/6 mice (7-9 weeks old) were purchased from Charles River (Canada) and maintained in the animal care facility at the University of Manitoba. The experimental protocol was approved by the University of Manitoba Animal Ethics Committee (10-073) and the research was conducted according to the Canadian Guidelines for Animal Research. Two groups of 4 and 6 mice were studied, one receiving the vehicle solution and one receiving intra-rectal Infusion of CTS for 6 days.

Peptide

CTS (Human $CgA_{352-372}$: SSMKLSFRARAYGFRGPG-PQL, SEQ ID NO:1)[23] was used (Biopeptide Co., Inc, San Diego, Calif.), and the peptide was injected intrarectally at 1.5 mg/per kg body weight per day for 6 days. Saline (0.9%) was injected in the control group. Mice were anaesthetized using Isoflurane (Abbott, Toronto, Canada). PE-90 tubing (10 cm long; ClayAdam, Parisppany, N.J.), which was attached to a tuberculin syringe (BD, Mississauga, Canada), was inserted 3.5 cm into the colon.

Assessment of Physical Condition

Weight loss, stool consistency and bleeding were assessed daily to determine any possible physical changes in the mice as a result of CTS treatment.[57] Scores were defined as follows: weight: 0, no loss; 1, 5-10%; 2, 10-15%; 3, 15-20%; and 4, 20% weight loss; stool: 0, normal; 2, loose stool; and 4, diarrhea; and bleeding: 0, no blood; 2, presence of blood; and 4, gross blood. Blood was assessed using the Hemoccult II test (Beckman Coulter, Oakville, Canada).

Fecal and Tissue Sample Collection

Samples were collected 6 days post-treatment induction, after euthanasia under isoflurane (Abbot) anaesthesia. The macroscopic score was determined on the sacrifice day based on stool consistency, rectal prolapse and rectal and colonic bleeding. On the day of sacrifice, a 250 mg fecal sample and a portion of the colon were collected in individual collector tubes from each animal. All samples were preserved at −80° C. before use.

DNA Extraction and Quality Check

Colons were opened and 50 mg of scrapings were taken from the inside. Samples were homogenized at room temperature, and genomic DNA was extracted from 250 mg fecal mass using a ZR fecal DNA Kit (Zymo Research Corp., Orange, Calif.). DNA extraction was performed using a Qiagen DNeasy blood & tissue kit (Qiagen corp, Valencia, USA). Both DNA extraction kits have a bead-beating step to lyse microbial cells. To match the concentration requirement for pyrosequencing, DNA quantity was determined using a Beckman DU/800 spectrophotometer (Beckman Coulter, Inc., Fullerton, Calif.). Genomic DNA was normalized to achieve a concentration of 20 ng/μL, and quality-checked by 16S rRNA gene using PCR amplification of 27F (5'-GAAGAGTTTGATCATGGCTCAG-3', SEQ ID NO:2) and 342R (5'-CTGCTGCCTCCCGTAG-3', SEQ ID NO:3)[58, 59]. Amplicons were verified by agarose gel electrophoresis.

Library Construction and Illumina Sequencing

Library construction and Illumina sequencing were performed as described by Derakhshani et al.[60]. Briefly, the V3-V4 region of the 16S rRNA gene was targeted for PCR amplification using modified F515/R806 primers[61]. A reverse PCR primer was Indexed with 12-base Golay barcodes to allow for sample multiplexing. The PCR reaction for each sample was performed in duplicate and contained 1.0 μl of pre-normalized DNA, 1.0 μl each of forward and reverse primers (10 μM), 12 μl HPLC grade water (Fisher Scientific, ON, Canada) and 10 μl 5 Prime Hot MasterMix® (5 Prime, Inc., Gaithersburg, USA). Reactions consisted of an initial denaturing step at 94° C. for 3 min followed by 35 amplification cycles at 94° C. for 45 sec, 50° C. for 60 sec and 72° C. for 90 sec; this was followed by an extension step at 72° C. for 10 min in an Eppendorf Mastercycler® (Eppendorf, Hamburg, Germany). PCR products were then purified using a ZR-96 DNA Clean-up Kit™ (ZYMO Research, CA, USA) to remove primers, dNTPs and reaction components. The V4 library was then generated by pooling 200 ng of each sample, and quantified using Picogreen dsDNA (Invitrogen, NY, USA). This was followed by multiple dilution steps using pre-chilled hybridization buffer (HT1) (Illumina, CA, USA) to bring the pooled ampilcons to a final concentration of 5 μM, and the concentration was measured through optical density using a Qubit® 2.0 Fluorometer (Life technologies, ON, Canada). Finally, 15% of the PhiX control library was spiked into the amplicon pool to improve the unbalanced and biased base composition, a known characteristic of low diversity 16S rRNA libraries. Customized sequencing primers for read1 (5'-TATGGTAATTGTGTGCCAGCMGCCGCGGTAA-3', SEQ ID NO:4), read2 (5'-AGTCAGTCAGCCGGAC-TACHVGGGTWTCTAAT-3', SEQ ID NO:5) and index read (5'-ATTAGAWACCCBDGTAGTCCGGCTGACT-GACT-3', SEQ ID NO:6) were synthesized and purified using polyacrylamide gel electrophoresis (Integrated DNA Technologies, IA, USA) and added to the MISeq Reagent Kit V2 (300-cycle) (Illumina, CA, USA). The 150 paired-end sequencing reaction was performed on a MISeq platform (Illumina, CA, USA) at the Gut Microbiome and Large Animal Biosecurity Laboratories, Department of Animal Science, University of Manitoba, Canada.

Bioinformatics Analyses

Bioinformatics analyses were performed as described by Derakhshani et al.[60]. Briefly, the PANDAseq assembler[62] was used to merge overlapping paired-end Illumina fastq files. All the sequences with mismatches or ambiguous calls in the overlapping region were discarded. The output fastq file was then analyzed using downstream computational pipelines in the open source software package QIIME[63]. Assembled reads were demultiplexed according to the barcode sequences and exposed to additional quality filters so that reads with more than 3 consecutive bases that had quality scores below $1e^{-5}$ were truncated, and those with a read length shorter than 75 bases were removed from the downstream analysis. Chimeric reads were filtered using UCHIME[64] and sequences were assigned to operational taxonomic units (OTU) using the QIIME Implementation of UCLUST[65] at the 97% pairwise identity threshold. Taxonomies were assigned to the representative sequence of each OTU using an RDP classifier[66] and aligned with the Greengenes core reference database[67] using PyNAST algorithms[68]. The phylogenetic tree was built with FastTree 2.1.3[69] for additional comparisons between microbial communities.

Alpha (α)- and Beta (β)-Diversity Analyses

Within-community diversity (α-diversity) was calculated using QIIME. An a rarefaction curve was generated using a Chao 1 estimator of species richness[70] with 10 sampling repetitions at each sampling depth. An even depth of approximately 15,700 sequences per sample was used for calculation of richness and diversity indices. To compare microbial composition between samples, β-diversity was measured by calculating the weighted and unweighted Unifrac distances[71] using QIIME default scripts. Principal coordinate analysis (PCoA) was applied on the resulting distance matrices to generate two-dimensional plots using PRIMER v6 software[72]. Permutational multivariate analysis of variance of Bray-Curtis distance (PERMANOVA)[73] was used to calculate P-values and test for significant differences in β-diversity among treatment groups. α-diversity differences between control and CTS groups were determined using SAS (SAS 9.3, 2012).

Partial Least Square Discriminant Analysis

Partial least square discriminant analysis (PLS-DA; SIMCA P+13.0, Umetrics, Umea, Sweden) was performed on the genus data to Identify the effects of treatments[74, 60]. The PLS-DA is a particular case of partial least square regression analysis in which Y is a set of variables describing the categories of a categorical variable on X. In this case, X variables were the bacterial genera and the Y variables were observations on different days. For this analysis, data were scaled using Unit Variance in SIMCA. Cross-validation was then performed to determine the number of significant PLS components and a permutation testing was conducted to validate the model. To avoid over-parameterization of the model, the variable Influence on the projection (VIP) value was estimated for each genus, and genera with VIP <0.50 were removed from the final model[75, 76]. An $r^2$ estimate then was used to evaluate the goodness of fit and $Q^2$ estimate was used to evaluate the predictive value of the model. The PLS-regression coefficients were used to identify genera that were most characteristic of each treatment group and the results were visualized by PLS-DA loading scatter plots.

Metagenomic Functional Prediction

Phylogenetic Investigation of Communities by Reconstruction of Unobserved States (PICRUSt), a computational approach to predict the functional composition of a metagenome using marker gene data and a database of reference genomes, was used on the Greengenes-selected OTUs to generate metagenomic data, and to derive relative Kyoto Encyclopedia of Genes and Genome (KEGG) pathway abundance. KEGG data were analyzed using Statistical Analysis of Metagenomic Profiles (STAMP).

Statistical Analysis

The SAS UNIVARIATE procedure (SAS 9.3, 2012) was used to test the normality of residuals for a biodiversity data. Non-normally distributed data were log transformed and then used to assess the effect of sampling using the SAS MIXED procedure. Phylum percentage data was also used to evaluate statistical differences among different days. The SAS MIXED procedure was used, as described above, to test for significant changes in the proportions of different phyla among the groups of Interest. All the phyla were divided into two groups of abundant (above 1% of the population) and low-abundance (below 1% of the population). The differences between groups were considered significant at $P<0.05$ while trends were observed at $P<0.1$.

The scope of the claims should not be limited by the preferred embodiments set forth in the examples but should be given the broadest Interpretation with the description as a whole.

TABLE 1

Relative abundance of bacterial phyla from pyrosequenced 16s rRNA sequences in fecal samples. A total of 328,085 sequences were generated after quality-filtering steps, with an average of 27,340.42 high-quality sequences per sample. This resulted in identification of 10 phyla. Of the 10 phyla, 4 phyla were considered as abundant within the population (≥1%), including Firmicutes, Bacteroidetes, Proteobacteria, and Deferribacteres. The other six phyla were considered less abundant within the population (<1%), including Actinobacteria, Cyanobacteria, Fibrobacteres, TM7, Tenericutes, and Verrucomicrobia.

| Phylum | Groups | Mean percentage of sequence in total bacterial population | Std. Error Mean |
|---|---|---|---|
| Unclassified | Control | 0.496921 | 0.092571 |
|  | CTS | 0.414249 | 0.04264 |
| Actinobacteria | Control | 0.511464 | 0.202226 |
|  | CTS | 0.187706 | 0.09371 |
| Bacteroidetes | Control | 59.59139 | 4.253899 |
|  | CTS | 73.99889 | 2.680188 |
| Cyanobacteria | Control | 0.017379 | 0.006038 |
|  | CTS | 0.152001 | 0.041196 |
| Deferribacteres | Control | 1.709693 | 1.021632 |
|  | CTS | 1.143747 | 0.782717 |
| Fibrobacteres | Control | 0.001941 | 0.00115 |
|  | CTS | 0.000541 | 0.000541 |
| Firmicutes | Control | 33.80289 | 3.56062 |
|  | CTS | 20.55645 | 1.827242 |
| Proteobacteria | Control | 2.218421 | 0.409325 |
|  | CTS | 2.872719 | 0.488761 |
| TM7 | Control | 0.003883 | 0.002301 |
|  | CTS | 0.003098 | 0.001035 |
| Tenericutes | Control | 0.314479 | 0.089961 |
|  | CTS | 0.404554 | 0.187125 |
| Verrucomicrobia | Control | 1.331539 | 0.730169 |
|  | CTS | 0.266048 | 0.129101 |

TABLE 2

Relative abundance of bacterial phyla from pyrosequenced 16s rRNA sequences in colonic mucosa associated samples A total of 207,123 sequences were generated after quality-filtering steps, with an average of 18,829.36 high-quality sequences per sample. This resulted in identification of 19 phyla. Of the 19 phyla, 4 phyla were considered as abundant within the population (≥1%), including Firmicutes, Bacteroidetes, Proteobacteria, and Deferribacteres. The other 15 phyla were considered less abundant within the population (<1%), including Acidobacteria, Actinobacteria, Armatimonadetes, Chlamydiae, Chlorobi, Cyanobacteria, Fibrobacteres, Lentisphaerae, OD1, OP3, Planctomycetes, Spirochaetes, TM7, Tenericutes, and Verrucomicrobia.

| Phylum | Groups | Mean percentage of sequence in total bacterial population | Std. Error Mean |
|---|---|---|---|
| Unclassified | Control | 0.122989 | 0.050167 |
|  | CTS | 0.291527 | 0.19307 |
| Acidobacteria | Control | 0.025735 | 0.010402 |
|  | CTS | 0.033388 | 0.00685 |
| Actinobacteria | Control | 0.095085 | 0.095085 |
|  | CTS | 0.072405 | 0.031928 |
| Armatimonadetes | Control | 0 | 0 |
|  | CTS | 0.000879 | 0.000879 |
| Bacteroidetes | Control | 8.06612 | 5.42359 |
|  | CTS | 21.0435 | 6.556034 |
| Chlamydiae | Control | 0 | 0 |
|  | CTS | 0.00306 | 0.002007 |
| Chlorobi | Control | 0 | 0 |
|  | CTS | 0.002098 | 0.002098 |
| Cyanobacteria | Control | 0.039247 | 0.022309 |
|  | CTS | 0.175241 | 0.063441 |
| Deferribacteres | Control | 6.923494 | 3.656936 |
|  | CTS | 5.949701 | 2.168418 |
| Fibrobacteres | Control | 0 | 0 |
|  | CTS | 0.013779 | 0.012973 |
| Firmicutes | Control | 10.13424 | 6.855156 |
|  | CTS | 12.51866 | 5.161134 |
| Lentisphaerae | Control | 0 | 0 |
|  | CTS | 0.00457 | 0.00457 |
| OD1 | Control | 0 | 0 |
|  | CTS | 0.004988 | 0.00332 |
| OP3 | Control | 0 | 0 |
|  | CTS | 0.001604 | 0.001604 |
| Planctomycetes | Control | 0.002067 | 0.002067 |
|  | CTS | 0.004664 | 0.001662 |
| Proteobacteria | Control | 72.02106 | 16.32041 |
|  | CTS | 59.16764 | 11.01085 |
| Spirochaetes | Control | 0 | 0 |
|  | CTS | 0.082258 | 0.082258 |
| TM7 | Control | 0 | 0 |
|  | CTS | 0.007409 | 0.00482 |
| Tenericutes | Control | 0.037096 | 0.019253 |
|  | CTS | 0.371448 | 0.170574 |
| Verrucomicrobia | Control | 2.532872 | 2.52412 |
|  | CTS | 0.142801 | 0.117295 |

REFERENCES

1. Davies J, Davies D. Origins and evolution of antibiotic resistance. Microbiol Mol Biol Rev 2010; 74:417-33.
2. Mullard A. New drugs cost US$2.6 billion to develop. Nature Reviews Drug Discovery 2014; 12:877.
3. Yu C G, Huang Q. Recent progress on the role of gut microbiota in the pathogenesis of Inflammatory bowel disease. J Dig Dis 2013.
4. Peterson D A, Frank D N, Pace N R, Gordon J I. Metagenomic approaches for defining the pathogenesis of inflammatory bowel diseases. Cell Host Microbe 2008; 3:417-27.
5. Kaser A, Zeissig S, Blumberg R S. Inflammatory bowel disease. Annu Rev Immunol 2010; 28:573-621.
6. Carding S, Verbeke K, Vipond D T, Corfe B M, Owen L J. Dysbiosis of the gut microbiota in disease. Microb Ecol Health Dis 2015; 262:6191.

7. Collins S M. A role for the gut microbiota in IBS. Nat Rev Gastroenterol Hepatol 2014; 11:497-505.
8. Kallus S J, Brandt U. The intestinal microbiota and obesity. J Clin Gastroenterol 2012; 46:16-24.
9. Raybould H E. Gut microbiota, epithelial function and derangements in obesity. J Physiol 2012; 590:441-6.
10. Vaishnava S, Behrendt C L, Ismail A S, Eckmann L, Hooper L V. Paneth cells directly sense gut commensals and maintain homeostasis at the Intestinal host-microbial Interface. Proc Natl Acad Sci USA 2008; 105:20858-63.
11. Stecher B, Hardt W D. The role of microbiota in infectious disease. Trends Microbiol 2008; 16:107-14.
12. Aral N, Mitomi H, Ohtani Y, Igarashi M, Kakita A, Okayasu I. Enhanced epithelial cell turnover associated with p53 accumulation and high p21WAF1/CIP1 expression in ulcerative colitis. Mod Pathol 1999; 12:604-11.
13. Renes I B, Verburg M, Van Nispen D J, Taminlau J A, Buller H A, Dekker J, Einerhand A W. Epithelial proliferation, cell death, and gene expression in experimental colitis: alterations in carbonic anhydrase I, mucin MUC2, and trefoil factor 3 expression. Int J Colorectal Dis 2002; 17:317-26.
14. Ostaff M J, Stange E F, Wehkamp J. Antimicrobial peptides and gut microblota in homeostasis and pathology. EMBO Mol Med 2013; 5:1465-83.
15. Khan W I, Ghia J E. Gut hormones: emerging role in immune activation and Inflammation. Clin Exp Immunol 2010; 161:19-27.
16. Norlen P, Curry W J, Bjorkqvist M, Maule A, Cunningham R T, Hogg R B, Haniott P, Johnston C F, Hutton J C, Hakanson R. Cell-specific processing of chromogranin A in endocrine cells of the rat stomach. J Histochem Cytochem 2001; 49:9-18.
17. Curry W J, Johnston C F, Hutton J C, Arden S D, Rutherford N G, Shaw C, Buchanan K D. The tissue distribution of rat chromogranin A-derived peptides: evidence for differential tissue processing from sequence specific antisera. Histochemistry 1991; 96:531-8.
18. Portela-Gomes G M, Stridsberg M. Selective processing of chromogranin A in the different islet cells in human pancreas. J Histochem Cytochem 2001; 49:483-90.
19. Portela-Gomes G M, Stridsberg M. Chromogranin A In the human gastrointestinal tract: an immunocytochemical study with region-specific antibodies. J Histochem Cytochem 2002; 50:1487-92.
20. Seidah N G, Chretien M. Proprotein and prohormone convertases: a family of subtllases generating diverse bioactive polypeptides. Brain Res 1999; 848:45-62.
21. Elden L E. Is chromogranin a prohormone? Nature 1987; 325:301.
22. Mahapatra N R, O'Connor D T, Vaingankar S M, Hikim A P, Mahata M, Ray S, Stalte E, Wu H, Gu Y, Dalton N, Kennedy B P, Ziegler M G, Ross J, Mahata S K. Hypertension from targeted ablation of chromogranin A can be rescued by the human ortholog. J Clin Invest 2005; 115:1942-52.
23. Mahata S K, Mahata M, Fung M M, O'Connor D T. Catestatin: a multifunctional peptide from chromogranin A. Regul Pept 2010; 162:33-43.
24. Mahata S K, O'Connor D T, Mahata M, Yoo S H, Taupenot L, Wu H, Gill B M, Parmer R J. Novel autocrine feedback control of catecholamine release. A discrete chromogranin a fragment is a noncompetitive nicotinic cholinergic antagonist. J Clin Invest 1997; 100:1623-33.
25. Briolat J, Wu S D, Mahata S K, Gonthier B, Bagnard D, Chasserot-Golaz S, Helle K B, Aunis D, Metz-Boutigue M H. New antimicrobial activity for the catecholamine release-inhibitory peptide from chromogranin A. Cell Mol Life Sci 2005; 62:377-85.
26. Boman H G, Agerberth B, Boman A. Mechanisms of action on *Escherichia coli* of cecropin P1 and PR-39, two antibacterial peptides from pig intestine. Infect Immun 1993; 61:2978-84.
27. Dorschner R A, Pestonjamasp V K, Tamakuwala S, Ohtake T, Rudisill J, Nizet V, Agerberth B, Gudmundsson G H, Gallo R L. Cutaneous injury induces the release of cathelicidin anti-microbial peptides active against group A *Streptococcus*. J Invest Dermatol 2001; 117:91-7.
28. Biancherl P, Di Sabatino A, Corazza G R, MacDonald T T. Proteases and the gut barrier. Cell Tissue Res 2013; 351:269-80.
29. Biswas N, Gayen J, Mahata M, Su Y, Mahata S K, O'Connor D T. Novel peptide isomer strategy for stable Inhibition of catecholamine release: application to hypertension. Hypertension 2012; 60:1552-9.
30. Rabbi M F, Labis B, Metz-Boutigue M H, Bernstein C N, Ghia J E. Catestatin decreases macrophage function in two mouse models of experimental colitis. Biochem Pharmacol 2014; 89:386-98.
31. Sciola V, Massironi S, Conte D, Caprioli F, Ferrero S, Ciafardini C, Peracchi M, Bardella M T, Piodi L. Plasma chromogranin a in patients with inflammatory bowel disease. Inflamm Bowel Dis 2009; 15:867-71.
32. Sidhu R, Drew K, McAlindon M E, Lobo A J, Sanders D S. Elevated serum chromogranin A in irritable bowel syndrome (IBS) and inflammatory bowel disease (IBD): a shared model for pathogenesis? Inflamm Bowel Dis 2010; 16:361.
33. Zissimopoulos A, Vradelis S, Konialis M, Chadollas D, Bampall A, Constantinidis T, Efremidou E, Kouklakis G. Chromogranin A as a biomarker of disease activity and biologic therapy in Inflammatory bowel disease: a prospective observational study. Scand J Gastroenterol 2014; 49:942-9.
34. Hooper L V, Stappenbeck T S, Hong C V, Gordon J I. Anglogenins: a new class of microbicidal proteins involved in innate Immunity. Nat Immunol 2003; 4:269-73.
35. Radek K A, Lopez-Garcia B, Hupe M, Niesman I R, Elias P M, Taupenot L, Mahata S K, O'Connor D T, Gallo R L. The neuroendocrine peptide catestatin is a cutaneous antimicrobial and Induced in the skin after injury. J Invest Dermatol 2008; 128:1525-34.
36. O'Connor D T, Frigon R P, Sokoloff R L. Human chromogranin A. Purification and characterization from catecholamine storage vesicles of human pheochromocytoma. Hypertension 1984; 6:2-12.
37. Bals R. Epithelial antimicrobial peptides in host defense against infection. Respir Res 2000; 1:141-50.
38. Aslam R, Atindehou M, Lavaux T, Haikel Y, Schneider F, Metz-Boutigue M H. Chromogranin A-derived peptides are involved in innate immunity. Curr Med Chem 2012; 19:4115-23.
39. Salzman N H, Hung K, Haribhai D, Chu H, Karlsson-Sjoberg J, Amir E, Teggatz P, Barman M, Hayward M, Eastwood D, Stoel M, Zhou Y, Sodergren E, Weinstock G M, Bevins C L, Williams C B, Bos N A. Enteric defensins are essential regulators of Intestinal microbial ecology. Nat Immunol 2010; 11:76-83.
40. Comito D, Casclo A, Romano C. Microbiota biodiversity in Inflammatory bowel disease. Ital J Pediatr 2014; 40:32.
41. Kelly D, Campbell J I, King T P, Grant G, Jansson E A, Coutts A G, Pettersson S, Conway S. Commensal anaerobic gut bacteria attenuate inflammation by regulating nuclear-cytoplasmic shuttling of PPAR-gamma and RelA. Nat Immunol 2004; 5:104-12.
42. Kamada N, Kim Y G, Sham H P, Valiance B A, Puente J L, Martens E C, Nunez G. Regulated virulence controls the ability of a pathogen to compete with the gut microbiota. Science 2012; 336:1325-9.
43. Borody T J, Warren E F, Leis S M, Surace R, Ashman O, Siarakas S. Bacteriotherapy using fecal flora: toying with human motions. J Clin Gastroenterol 2004; 38:475-83.
44. Borody T J, George L, Andrews P, Brandl S, Noonan S, Cole P, Hytand L, Morgan A, Maysey J, Moore-Jones D. Bowel-flora alteration: a potential cure for inflammatory bowel disease and irritable bowel syndrome? Med J Aust 1989; 150:604.
45. Nagalingam N A, Kao J Y, Young V B. Microbial ecology of the murine gut associated with the development of dextran sodium sulfate-induced colitis. Inflamm Bowel Dis 2011; 17:917-26.
46. Derrien M, Vaughan E E, Plugge C M, de Vos W M. Akkermansia muciniphila gen. nov., sp. nov., a human Intestinal mucin-degrading bacterium. Int J Syst Evol Microbiol 2004; 54:1469-76.
47. Kelly D, Mulder I E. Microbiome and Immunological interactions. Nutr Rev 2012; 70 Suppl 1:S18-30.
48. Salyers A A. Bacteroides of the human lower intestinal tract. Annu Rev Microbiol 1984; 38:293-313.
49. Wexler H M. Bacteroides: the good, the bad, and the nitty-gritty. Clin Microbiol Rev 2007; 20:593-621.
50. Mazmanian S K, Kasper D L The love-hate relationship between bacterial polysaccharides and the host immune system. Nat Rev Immunol 2006; 6:849-58.
51. Round J L, Mazmanian S K. Inducible Foxp3+ regulatory T-cell development by a commensal bacterium of the intestinal microbiota. Proc Natl Acad Sd USA 2010; 107:12204-9.
52. Chistoserdovai L. Functional metagenomics: recent advances and future challenges. Biotechnol Genet Eng Rev 2010; 26:335-52.
53. Hodges K, Gill R. Infectious diarrhea: Cellular and molecular mechanisms. Gut Microbes 2010; 1:4-21.
54. Schrott-Fischer A, Bitsche M, Humpel C, Walcher C, Maler H, Jellinger K, Rabl W, Glueckert R, Marksteiner J. Chromogranin peptides in amyotrophic lateral sclerosis. Regul Pept 2009; 152:13-21.
55. Vaarala O. Gut microblota and type 1 diabetes. Rev Diabet Stud 2013; 9:251-9.
56. Stadinski B D, Delong T, Reisdorph N, Relsdorph R, Powell R L, Armstrong M, Piganelli J D, Barbour G, Bradley B, Crawford F, Marrack P, Mahata S K, Kappler J W, Haskins K. Chromogranin A is an autoantigen in type 1 diabetes. Nat Immunol 2010; 11:225-31.
57. Cooper H S, Murthy S N, Shah R S, Sedergran D J. Clinicopathologic study of dextran sulfate sodium experimental murine colitis. Lab Invest 1993; 69:238-49.
58. Sepehri S, Kotlowski R, Bernstein C N, Krause D O. Microbial diversity of Inflamed and noninflamed gut biopsy tissues in inflammatory bowel disease. Inflamm Bowel Dis 2007; 13:675-83.
59. Khafipour E, Li S, Plaizier J C, Krause D O. Rumen microbiome composition determined using two nutritional models of subacute ruminal acidosis. Appl Environ Microbiol 2009; 75:7115-24.
60. Derakhshani H, Alqami S, Cardoso F C, Khazanehel H R, Khafipour E, Plaizler J C, Loor J J. The microbiome composition of the rumen is altered during the peripartal period in dairy cattle. PoS One 2014; In press.
61. Caporaso J G, Lauber C L, Walters W A, Berg-Lyons D, Huntley J, Fierer N, Owens S M, Betley J, Fraser L, Bauer M. Ultra-high-throughput microbial community analysis on the Illumina HISeq and MiSeq platforms. The ISME journal 2012; 6:1621-1624.
62. Masella A, Bartram A, Truszkowsk J, Brown D, Neufeld J. PANDAseq: paired-end assembler for illumina sequences. BMC Bioinformatics 2012; 13:1-7.
63. Caporaso J G, Kuczynski J, Stombaugh J, Bittinger K, Bushman F D, Costello E K, Fierer N, Pena A G, Goodrich J K, Gordon J I. QIIME allows analysis of high-throughput community sequencing data. Nature methods 2010; 7:335-336.
64. Edgar R C, Haas B J, Clemente J C, Quince C, Knight R. UCHIME improves sensitivity and speed of chimera detection. Bioinformatics 2011; 272194-2200.
65. Edgar R C. Search and clustering orders of magnitude faster than BLAST. Bioinformatics 2010; 26:2460-2461.
66. Wang Q, Garrity G M, Tiedje J M, Cole J R. Naive Bayesian classifier for rapid assignment of rRNA sequences into the new bacterial taxonomy. Applied and environmental microbiology 2007; 73:5261-5267.
67. DeSantis T Z, Hugenholtz P, Larsen N, Rojas M, Brodie E L, Keller K, Huber T, Dalevi D, Hu P, Andersen G L. Greengenes, a chimera-checked 16S rRNA gene database and workbench compatible with ARB. Applied and environmental microbiology 2006; 72:5069-5072.
68. Caporaso J G, Bittinger K, Bushman F D, DeSantis T Z, Andersen G L, Knight R. PyNAST: a flexible tool for aligning sequences to a template alignment. Bioinformatics 2010; 26266-267.
69. Price M N, Dehal P S, Arkin A P. FastTree 2-approximately maximum-likelihood trees for large alignments. PloS one 2010; 5:e9490.
70. Chao A. Nonparametric estimation of the number of classes in a population. Scandinavian Journal of statistics 1984:265-270.
71. Lozupone C, Knight R. UniFrac: a new phylogenetic method for comparing microbial communities. Applied and environmental microbiology 2005; 71:8228-8235.
72. Warwick R, Clarke K. PRIMER 6. PRIMER-E Ltd, Plymouth 2006.
73. Anderson M. PERMANOVA: a FORTRAN computer program for permutational multivariate analysis of variance. Department of Statistics, University of Auckland, New Zealand 2005; 24.
74. Li R, Khafipour E, Krause D O, Entz M H, de Kievit T R, Fernando W D. Pyrosequencing reveals the influence of organic and conventional farming systems on bacterial communities. PloS one 2012; 7:e51897.
75. Verhulst N O, Qiu Y T, Beijleveld H, Maliepaard C, Knights D, Schulz S, Berg-Lyons D, Lauber C L, Verduijn W, Haasnoot G W. Composition of human skin microblota affects attractiveness to malaria mosquitoes. PloS one 2011; 6:e28991.
76. Pérez-Enciso M, Tenenhaus M. Prediction of clinical outcome with microarray data: a partial least squares discriminant analysis (PLS-DA) approach. Human genetics 2003; 112:581-592.

The invention claimed is:

1. A method for increasing levels of Bacteriodetes relative to levels of other bacteria in the gut of an individual in need of such treatment comprising administering to said individual an effective amount of catestatin (CTS).

2. The method according to claim 1 wherein the individual in need of such treatment is an individual whose gut microbiota is in a dysbiotic state or who is thought to have developed dysbiosis or is at risk of developing dysbiosis.

3. The method according to claim 2 wherein the individual developed dysbiosis as a result of a treatment or as a result of being subjected to a diet or as a result of environmental conditions.

4. The method according to claim 1 wherein the individual in need of such treatment is an individual who is at risk of developing type 1 diabetes, type 2 diabetes, obesity, IBS or IBD either as a result of heredity, genetic predisposition and/or lifestyle.

5. The method according to claim 4 wherein the administration of catestatin prophylactically treats IBD or IBS.

6. The method according to claim 5 wherein the IBD or IBS is treated prophylactically with the proviso that symptoms other than inflammation are being treated.

7. The method according to claim 4 wherein the administration of catestatin prophylactically treats obesity, type 1 diabetes or type 2 diabetes.

8. A method for decreasing relative levels of Firmicutes relative to other bacteria in the gut of an individual in need of such treatment comprising administering to said individual an effective amount of catestatin (CTS).

9. The method according to claim 8 wherein the individual in need of such treatment is an individual whose gut microbiota is in a dysbiotic state or who is thought to have developed dysbiosis or is at risk of developing dysbiosis.

10. The method according to claim 9 wherein the individual developed dysbiosis as a result of a treatment or as a result of being subjected to a diet or as a result of environmental conditions.

11. The method according to claim 8 wherein the individual in need of such treatment is an individual who is at risk of developing type 1 diabetes, type 2 diabetes, obesity, IBS or IBD either as a result of heredity, genetic predisposition and/or lifestyle.

12. A method of modulating gut microbiota composition comprising administering to an individual in need of such treatment an effective amount of catestatin (CTS).

13. The method according to claim 12 wherein the individual in need of such treatment is an individual whose gut microbiota is in a dysbiotic state or who is thought to have developed dysbiosis or is at risk of developing dysbiosis.

14. The method according to claim 13 wherein the individual developed dysbiosis as a result of a treatment or as a result of being subjected to a diet or as a result of environmental conditions.

15. The method according to claim 12 wherein the individual in need of such treatment is an individual who is at risk of developing type 1 diabetes, type 2 diabetes, obesity, IBS or IBD either as a result of heredity, genetic predisposition and/or lifestyle.

16. The method according to claim 15 wherein the administration of catestatin prophylactically treats IBD or IBS.

17. The method according to claim 16 wherein the IBD or IBS is treated prophylactically with the proviso that symptoms other than inflammation are being treated.

18. The method according to claim 15 wherein the administration of catestatin prophylactically treats obesity, type 1 diabetes or type 2 diabetes.

* * * * *

SEQUENCE LISTING

<160> NUMBER OF SEQ ID NOS: 6

<210> SEQ ID NO 1
<211> LENGTH: 21
<212> TYPE: PRT
<213> ORGANISM: artificial sequence
<220> FEATURE:
<223> OTHER INFORMATION: catestatin, derived from amino acids 352-372 of human chromogranin A

<400> SEQUENCE: 1

Ser Ser Met Lys Leu Ser Phe Arg Ala Arg Ala Tyr Gly Phe Arg Gly
1               5                   10                  15

Pro Gly Pro Gln Leu
            20

<210> SEQ ID NO 2
<211> LENGTH: 22
<212> TYPE: DNA
<213> ORGANISM: artificial sequence
<220> FEATURE:
<223> OTHER INFORMATION: 16S rRNA forward amplification primer

<400> SEQUENCE: 2
gaagagtttg atcatggctc ag                                          22

<210> SEQ ID NO 3
<211> LENGTH: 16
<212> TYPE: DNA
<213> ORGANISM: artificial sequence
<220> FEATURE:
<223> OTHER INFORMATION: 16S rRNA reverse amplification primer

<400> SEQUENCE: 3
ctgctgcctc ccgtag                                                 16

<210> SEQ ID NO 4
<211> LENGTH: 31
<212> TYPE: DNA
<213> ORGANISM: artificial sequence
<220> FEATURE:
<223> OTHER INFORMATION: 16S rRNA sequencing primer

<400> SEQUENCE: 4
tatggtaatt gtgtgccagc mgccgcggta a                                31

<210> SEQ ID NO 5
<211> LENGTH: 32
<212> TYPE: DNA
<213> ORGANISM: artificial sequence
<220> FEATURE:
<223> OTHER INFORMATION: 16S rRNA sequencing primer

<400> SEQUENCE: 5
agtcagtcag ccggactach vgggtwtcta at                               32

<210> SEQ ID NO 6
<211> LENGTH: 32
<212> TYPE: DNA
<213> ORGANISM: artificial sequence
<220> FEATURE:
<223> OTHER INFORMATION: 16S rRNA sequencing primer

<400> SEQUENCE: 6
attagawacc cbdgtagtcc ggctgactga ct                               32